United States Patent [19]

Hamano et al.

[11] 4,038,278
[45] July 26, 1977

[54] 4-AMINOPYRIMIDIUM DERIVATIVES AND PREPARATION THEREOF

[75] Inventors: Sachiyuki Hamano, Tokyo; Takaharu Nakamura, Shounan, both of Japan

[73] Assignee: Eisai Co., Ltd., Tokyo, Japan

[21] Appl. No.: 603,235

[22] Filed: Aug. 8, 1975

[30] Foreign Application Priority Data

Aug. 9, 1974  Japan ................................. 49-90783

[51] Int. Cl.$^2$ .......................................... C07D 239/26
[52] U.S. Cl. ...................... 260/256.4 N; 260/256.5 R; 424/251
[58] Field of Search ................. 260/256.4 N, 256.5 R; 424/251

[56] References Cited
PUBLICATIONS

Rodd Chem. of Carbon Compounds, vol. IV, Part A, Heterocyclic Compounds Elsevier (1957), pp. 510 & 511.
Otiai et al., "Chem. Abstracts," vol. 33 (1939), col. 3791$^9$, Abstract of J. Pharm. Soc., Japan, 59, pp. 18-28 (1939).

Primary Examiner—Donald G. Daus
Assistant Examiner—D. B. Springer
Attorney, Agent, or Firm—Wenderoth, Lind & Ponack

[57] ABSTRACT

New 4-aminopyrimidium derivatives of the general formula:

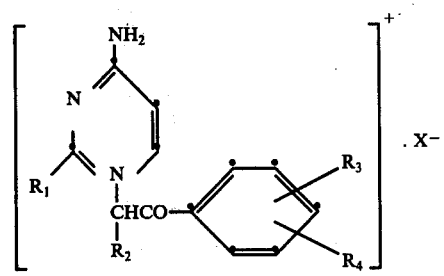

wherein $R_1$ and $R_2$ each represents a hydrogen atom or a lower alkyl group, and $R_3$ and $R_4$ each represents a hydrogen or halogen atom, a lower alkyl, a lower alkoxyl, a lower alkoxycarbonyl, a lower alkylsulfonyl, nitro or amino group, and X represents a halogen atom, as well as a process for the preparation thereof. The compounds are useful as anti-inflammatory, analgesic agents without producing gastrointestinal trouble.

4 Claims, 1 Drawing Figure

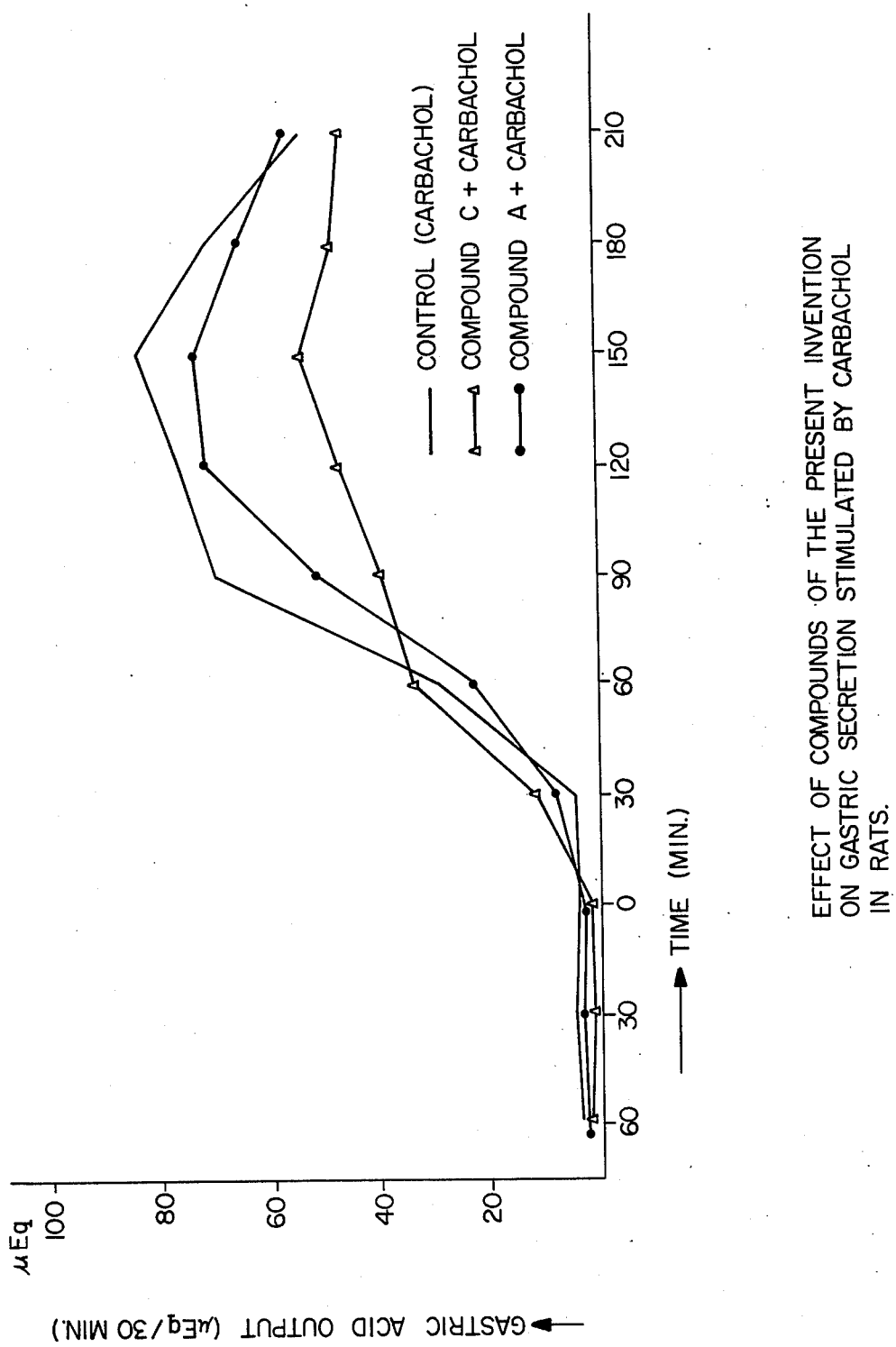

4-AMINOPYRIMIDIUM DERIVATIVES AND PREPARATION THEREOF

The present invention relates to new 4-aminopyrimidine derivatives useful as medicaments. More particularly, the present invention relates to the new 4-aminopyrimidium derivatives having the general formula (I)

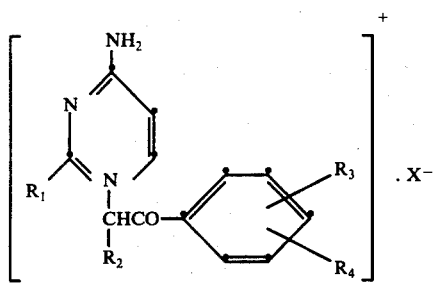

(I)

wherein $R_1$ and $R_2$ each represents a hydrogen atom or a lower alkyl group, and $R_3$ and $R_4$ each represents a hydrogen or a halogen atom, a lower alkyl, a lower alkoxyl, a lower alkoxycarbonyl, a lower alkylsulfonyl, nitro or amino group, and X represents a halogen atom, and the preparation thereof. The new compounds (I) of the present invention exhibit outstanding anti-inflammatory and analgesic activities. It has further been recgonized by the characteristic features of these compounds that they produce little gastrointestinal trouble. Therefore, these compounds are useful as non-steroidal, anti-inflammatory and analgesic agents suitable for the treatment of diseases such as, articular rheumatism, arthritis, spondylitis, tendinitis, fracture, distortion, post-operative inflammation, olitis media, nasosinusitis, neuralgia, lumbago, rachialgia, odontalgia, neuritis, pharyngitis, laryngitis, arthritis urica and the like.

As non-steroidal analgesic and anti-inflammatory agents, the compounds of the indole and pyrazole series have hitherto been broadly employed. However, since administration of those known compounds often produces injurious side effects, for example peptic ulcers, they are not adapted for consecutive administration for extended periods of time. Nor are they suitable for administration to patients suffering from peptic ulcers such as gastric ulcers and duodenal ulcers.

Our study has been directed to the development of anti-inflammatory agents capable of consecutive administrative for an extended period of time without producing injurious side-effects. Thus, these agents are adapted for administration to a patient that cannot endure the administration of a severe anti-inflammatory agent or to a patient with chronic inflammation who requires consecutive administrations for an extended period of time.

In order to attain the abovementioned agents, the present inventors have devoted themseleves to an investigation of various compounds.

As a result of these investigations, it has been found that 4-aminopyrimidium derivatives having the general formula (I)

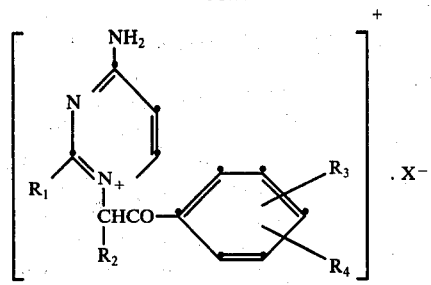

(I)

wherein $R_1$ and $R_2$ each represents a hydrogen atom or a lower alkyl group, and $R_3$ and $R_4$ each represents a hydrogen or a halogen atom, a lower alkyl, a lower alkyoxyl, a lower alkoxycarbonyl, a lower alkylsulfonyl, nitro or amino group, and X represents a halogen atom, are thus a useful anti-inflammatory analgesic agents capable of consecutive administrations for an extended period of time.

Accordingly, one of the objectives of the present invention is to provide a new anti-inflammatory and analgesic agent.

Another objective of this invention is to provide a new anti-inflammatory agent which produces no injurious side-effects and which is adapted for consecutive administration for an extended period of time.

A further objective of this invention is to provide a process for producing the said new anti-inflammatory agent.

A still further objective of this invention is to provide a therapeutic composition which contains the said new compounds as the active ingredient therefor in order to provide relief from pain of inflammation, swelling, fever and the like in humans.

Another objective of this invention is to provide a method for treating the aforementioned inflammations in man.

The process for the preparation of the particular compounds accomplished in the present invention is carried out in accordance with the following reaction schema:

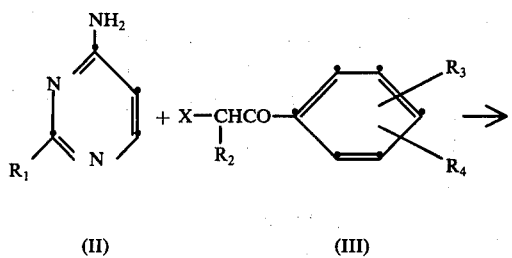

(II)    (III)

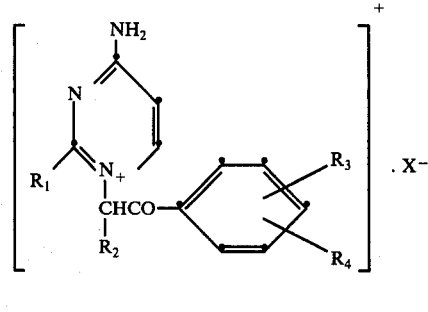

(I)

wherein $R_1$, $R_2$, $R_3$, $R_4$ and X have the same meanings as defined above.

The new compounds of the present invention can be obtained by dissolving 2-substituted 4-aminopyrimidine (II) in a solvent selected from the group consisting of ether such as dimethoxyethane, diethylether, isopropylether and the like; in amides such as dimethylformamide, dimethylacetamide and the like; in alcohols such as methanol, ethanol and the like; and by dissolving compound (II) in aromatics such as benzenes, toluene, xylene and the like, and then mixing the resulting solution with α-benzoyl alkylhalide (III) to react under reflux.

The new compounds of the present invention exhibit anti-inflammatory and analgesic activities and produce little gastrointestinal trouble. These facts are proven by the following data which was obtained by the following pharmacological tests.

PHARMACOLOGICAL TEST (I)

The test compounds
  i. Control: Aspirin (hereinafter referred to "Control compound")
  ii. The compounds of the present invention; 4-aminopyrimidine $N^1$-(p-methoxyphenacyl)bromide (hereinafter referred to "Compound A of the present invention"), and 4-aminopyrimidine $N^1$-(m-methylphenacyl)bromide (hereinafter referred to "Compound B of the present invention")

Dose: 100 mg/Kg

Test animal: For the respective compounds, four male rats of the Wistar strain weighing approximately 150g were used. The test animals were made to fast for approximately 16 hours.

Test items

1. Anti-edematic effects

The anti-edematic test is carried out by determining the increase of edema due to the injection of a physioloical salt solution, in accordance with the paw edema method. [see Winter. C. A. et al ; Proc. Soc. exp. Biol. Med. 111, 544 (1962)].

The test compounds were respectively suspended in five percent of aqueous solution of gum Arabic, and the suspensions were orally administered to the rats one hour before the injection of the Carrageenin. Activities were determined by measuring the volume of the hind paw of the rat three hours after the administration of the Carrageenin.

TABLE 1

| Test Compounds | Oral dose (mg-/kg) | Results Anti-edematic ratio (%) | Comparison with Control Compound |
|---|---|---|---|
| Control Compound | 100 | 35.8 | 100 |
| Compound A of the present invention | 100 | 50.0 | 140 |
| Compound B of the present invention | 100 | 35.3 | 99 |

2. Degree of gastric trouble

The rats used in above test of anti-edematic effects were slaughtered, and their stomachs were visibly observed in accordance with the under-mentioned bases. Measurement values were decided by summing up the respective data of 4 tests of each group.

| Basis for scoring the degree of gastric trouble | |
|---|---|
| Visible observation of the stomach mucosa | Score |
| No abnormality is recognized | 0 |
| Slight edema, congestion or slight erosion | 1 |
| Scattered or limitted erosion and spotted bleeding | 2 |
| Heavy erosion, linear bleeding or enlarged bleeding | 3 |

Heavy erosion, linear bleeding or enlarged bleeding

TABLE 2

| Results Compounds | Degree of gastric trouble |
|---|---|
| Control compound | 12 |
| Compound A of the present invention | 2 |
| Compound B of the present invention | 6 |

From the results of above measurements 1) and 2), it was observed that each anti-edematic ratio of Compound A and Compound B of the present invention are both equal to, or more than that of the Control compound. It was also found that each degree of gastric trouble of the Compound A and Compound B were both extremely less than that of the Control compound.

From the results of the foregoing measurement results of pharmacological activites, it was found that the new compounds of the present invention have excellent anti-inflammatory effects and produce little gastric trouble.

The followings are experiments of analgesic activites utilizing the compounds of the present invention.

PHARMACOLOGICAL TEST (II)

i. Method for Experiment

Comparative tests for anti-acetic acid Writhing activity in mice were made to the Compound A of the present invention and 4-amino-pyrimidine-$N^1$-phenacyl-bromide (hereinafter referred to as Compound C), using Aspirin as a control compound. The test compounds were respectively suspended in an of aqueous solution of containing five percent of gum Arabic. Eight male mice of dd strain weighing approximately 20 - 23g were used as the test animals. The mice were made to fast for about 19 hours.

After 50 minutes or 170 minutes of administration of the test compounds, 0.1 ml of 0.7% acetic acid solution per 10 g. of the body weight of the test animal was injected intraperitoneally. Regarding the expansion of the hind paw of the mice induced during 15 minutes after the injection, a number of Writhing syndromes were encountered and recorded. Effects of the respective test compounds against the usual behavior the of mice were also observed. In the above test, 5% gum arabic solution per se was administered to the control animal.

ii. Results of Experiment

Various doses of the respective compounds were orally administered to eight mice. After 1 or 3 hours of the administration, a anti-acetic acid Writhing test was carried out. The resulting data is listed in the following Table 3.

Table 3

Anti-acetic acid Writhing effect in mice

| Test Compound | Dose mg/Kg | 1hr No. of Writhing Syndrome (m±S.E.) | 1hr % of Protection | 3hr No. of Writhing Syndrome (m±S.E.) | 3hr % of Protection |
|---|---|---|---|---|---|
| Control |  | 40.3 ± 1.9 | 0 | 30.6 ± 2.3 | 0 |
| Compound A | 20 | 41.4 ± 5.6 | −3 | 34.6 ± 5.4 | −13 |
|  | 40 | 33.1 ± 3.7 | 18 | 17.6 ± 4.8 | 43 |
|  | 80 | 46.3 ± 3.6 | −15 | 23.1 ± 6.6 | 25 |
|  | 160 | 29.4 ± 5.1 | 27* | 21.8 ± 4.0 | 29 |
|  | 320 | 17.1 ± 4.6 | 58** | 3.8 ± 2.7 | 88** |
| Compound C | 20 | 36.9 ± 3.6 | 8 | 41.4 ± 5.0 | −35 |
|  | 40 | 34.9 ± 7.3 | 13 | 22.3 ± 5.3 | 27 |
|  | 80 | 45.3 ± 1.7 | −12 | 36.4 ± 3.8 | −19 |
|  | 160 | 29.9 ± 5.1 | 26* | 11.0 ± 3.3 | 64** |
|  | 320 | 15.9 ± 5.5 | 61** | 12.9 ± 4.6 | 58** |

**P<0.01
*P<0.05

Table 4

Oral administration

| Test Compound | Dose (mg/Kg) | Number | Ulcer Index(mm) | Inhibitory % |
|---|---|---|---|---|
| Control |  | 6 | 51.6 ± 3.3 | — |
| Compound A | 150 | 6 | 37.1 ± 5.9 | 28.1 |
|  | 300 | 6 | 15.3 ± 6.1** | 70.3 |
| Control |  | 6 | 69.3 ± 2.1 | — |
| Compound C | 150 | 6 | 53.1 ± 5.8* | 23.4 |
|  | 300 | 6 | 23 ± 6.3* | 66.2 |
| Control |  | 6 | 69.5 ± 3.1 | — |
| Propantheline | 15 | 6 | 43.8 ± 12.9 | 37.0 |
|  | 30 | 6 | 26.8 ± 7.4** | 61.4 |

*P<0.05
**P<0.01 ii. Effect on gastric secretion in 4hr. pylorus-ligated rats. (Intraduodenal administration)

Table 5

| Test Compound | Dose (mg/μg) | Number | Vol/100 g B.W.(ml) | Inhibitory % | Titrable acidity to PH 7.0 (μEq/100g B.W.) | Inhibitory % |
|---|---|---|---|---|---|---|
| Control |  | 6 | 2.02 ± 0.22 |  | 188.4 ± 23.0 |  |
| Compound A | 150 | 5 | 0.5 ± 0.06** | 73.3 | 14.4 ± 4.2** | 92.4 |
|  | 300 | 5 | 0.72 ± 0.24** | 64.4 | 6.8 ± 3.4** | 96.4 |
| Compound C | 150 | 5 | 0.94 ± 0.20** | 53.5 | 57.0 ± 22.4** | 69.7 |
|  | 300 | 6 | 0.62 ± 0.08 | 69.3 | 22.2 ± 7.6 | 88.2 | pH of the test compound :
Compound A : 6.3
Compound C : 5.8
**P<0.01

From the results of the comparison concerning anti-acetic acid Writhing activities in mice as mentioned above, it was observed that the compounds of the present invention have analgesic activities which are almost equal to these of Aspirin.

More particularly, it is confirmed from the above experiments that the compounds of the present invention exhibit anti-acetic acid Writhing activities at 160 - 320 mg/ug p. o. The control activites of the compound of the present invention are almost equivalent or somewhat more intense to those of Aspirin [ED$_{50}$ 410mg/Kg (1hr.) and 253 mg/Kg (3 hr.)]

As stated above, the compounds of the present invention are anti-inflammatory and analgesic agents having anti-ulcer activities. The anti-ulcer activites are shown by pharmacological test (III).

PHARMACOLOGICAL TEST (III)

Using rats of Wistar strain as test animals weighing about 150 - 160 g., the anti-ulcer activities were measured in accordance with the conventional manner with respect to the following four (4) items.

i. Stress Ulcer (Immersion) at 23° - 25° C. for 20 hrs.

The results are shown in Table 4. From the Table 4, it has been proven that both Compounds A and C are effective at 300 mg/Kg.(p.o.).

From the Table 5, it is apparent that the remarkable inhibitory effect on gastric secretion was shown at dosages of 150 and 300 mg/Kg, respectively.

iii. Effect on Shay Ulcer in rats. (Method by 17hr. pylorusligated rats)

The results are shown in Tables 6 and 7.

Table 6

| Test Compound | Dose (mg/μg) | Number | Ulcer Index (mm) | Inhibitory % |
|---|---|---|---|---|
| Control |  | 6$^a$ | 54 ± 14 | — |
| Compound A | 300 | 2 | 42(0),(84) | 23.4 |
| Compound C | 300 | 6 | 19 ± 7* | 64.8 |

*P<0.05

Table 7

| Test Compound | Number | Vol(ml) 100g B.W. | Inhibitory | Titrable Acidity to pH 7.0(μEq/ 100g B.W.) | Inhibitory % |
|---|---|---|---|---|---|
| Control | 5$^a$ | 4.79 ± 0.43 | — | 347.8 ± 78.6 | — |
| Compound A | 2$^b$ | 2.20(1.11) (3.29) | 54.1 | 188.2 ± 72.0 | 45.9 |
| Compound C | 6 | 3.14 ± 0.43* | 34.5 | 414.8 ± 83.0 | −19.3 | pH values of the respective test compounds are adjusted to 7.0.
$^a$ Difference between the number in Table 6 and that in Table 7 is due to perforation in one animal which resulted in the impossibility of measuring the gastric juice.
$^b$ Only four animals died in the case wherein Compound A was used, but the cause of death was not due to perforation.

From Tables 6 and 7, it was shown that both Compounds A and C exhibit outstanding inhibitory effects against the appearance of ulcer.

iv. Effect on gastric secretion in acute gastric fistula rats.

Comparative tests were carried out to measure the effects on gastric secretion stimulated by carbachol and the effects of Compounds A and C on eight rats of Wistar strain. The results are graphically shown in the accompanying FIG. 1. It is confirmed from FIG. 1 that, especially, Compound C shows about 35% inhibitory effect to Maximum Response.

By means of the above-mentioned pharmacological experiments, the compounds of the present invention are new non-steroidal anti-inflammatory and analgesic agents having anti-ulcer activity, and represent a new type of medicine utterly different from conventional medicines. In other words, almost all of the conventional anti-inflammatory, analgesic compounds are accompanied by gastro intestinal trouble such as peptic ulcer and the like. For these reasons, it was impossible to continuously administer the medicines to chronic patients. Moreover, administration could not be done to patients suffering from peptic ulcers. Since the present invention has overcome these drawbacks, the invention can be said to be one of epochproportions. Therefore, these compounds are useful as nonsteroidal anti-inflammatory and analgesic agents suitable for the treatment of diseases such as, articular rheumatism, arthritis, spondylitis, tendinitis, fracture, distortion, postoperative inflammation, olitis media, nasosinusitis, neuralgia, lumbago, rochialgia, odontalgia, neuritis, pharynaitis, laryngitis, gout and the like.

The following Examples illustrate the present invention.

EXAMPLE 1

Preparation of 4-aminopyrimidine $N^1$-(p-methoxyphenacyl) bromide

One gram (0.01 mol) of 4-aminopyrimidine is mixed with 30 ml. of ethanol. The mixture is stirred to dissolve the whole. To the resulting solution, there is added 2.3g (0.01 mol) of p-methoxy-ω-bromoacetophenone, and the mixture is subjected to reaction under reflux for 30 minutes. After cooling the mixture with ice, the crystalline product separated out is recovered by filtration. The product is then rinsed with a small quantity of ethanol, and recrystallized from an aqueous ethanol. There is thus obtained 0.8g (yield: 24.7%) of the intended product. The product has a melting point of 242° – 243° C with decomposition.

Elementary analysis of the product having the presumptive formula $C_{15}H_{14}N_3O_2Br$ gave the following results:

|  | C | H | N |
|---|---|---|---|
| Calculated (%) | 48.15 | 4.30 | 12.96 |
| Found (%) | 47.82 | 4.40 | 12.94 |

EXAMPLE 2

Preparation of 4-aminopyrimidine $N^1$-(m-methylphenacyl) bromide

One gram (0.01 mol) of 4-aminopyrimidine is mixed with 30 ml. of 2-dimethoxyethane. The mixture is heated at the temperature of from 60° C. to 70° C. to result in dissolution.

To the solution, there is added 2.2g of m-methyl-ω-bromoacetophenone and the mixture is subjected to reaction at a temperature of from 65° C. to 70° C. for 30 minutes. The reaction mixture is then allowed to cool on ice. The crystalline substance separated out is recovered by filtration, which is rinsed with a small quantity of ethanol, and then recrystallized from an aqueous ethanol. There is thus obtained 1.3g (yield: 42.2%) of the intended product. The product has a melting point of 256° – 258° C. with decomposition.

Elementary analysis of the product having the presumptive formula $C_{13}H_{14}N_3OBr$ gave the followings:

|  | C | H | N |
|---|---|---|---|
| Calculated (%) | 50.65 | 4.57 | 13.63 |
| Found (%) | 50.29 | 4.57 | 13.80 |

EXAMPLE 3

Preparation of 4-aminopyrimidine $N^1$-phenacyl bromide

One gram (0.01 mol) of 4-aminopyrimidine is mixed with 30 ml. of ethanol. The mixture is stirred to dissolve it. To the resulting solution, there is added 1.99g (0.01 mol) of ω-bromoacetophenone and the mixture is subjected to reaction under reflux for 30 minutes. The resulting solution is clear initially, and crystalline product is immediately separated out.

The resulting crystalline product is allowed to cool with ice, and recovered by filtration. The crystalline product is rinsed with a small quantity of ethanol and then recrystallized from an aqueous ethanol. There is thus obtained 1.3g (yield: 44.2%) of the final product. The product has a melting point of 292° – 293° C. with decomposition.

Elementary analysis of the product having the presumptive formula $C_{12}H_{12}N_3OBr$ gave the followings:

|  | C | H | N |
|---|---|---|---|
| Calculated (%) | 48.99 | 4.12 | 14.29 |
| Found (%) | 49.20 | 4.11 | 14.53 |

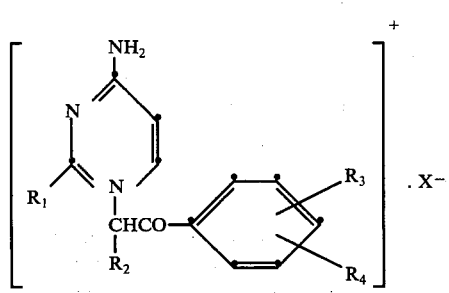

(I)

| Ex. Nos. | $R_1$ | $R_2$ | $R_3$ | $R_4$ | X | Molecular Formula Melting Point (° C) | Calcurated (%) C | H | N | Found (%) C | H | N |
|---|---|---|---|---|---|---|---|---|---|---|---|---|
| 4 | H | H | p-SO$_2$CH$_3$ | H | Br | C$_{13}$H$_{14}$N$_3$O$_3$SBr<br>292 – 293 (Decomp.) | 41.95 | 3.80 | 11.29 | 41.99 | 3.76 | 11.30 |

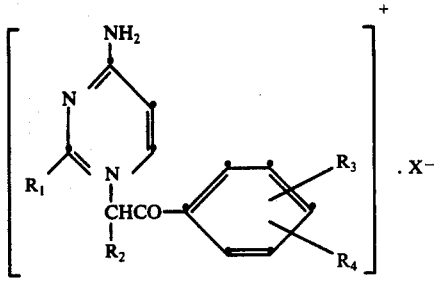

(I)

| Ex. Nos. | $R_1$ | $R_2$ | $R_3$ | $R_4$ | X | Molecular Formula Melting Point (° C) | Calcurated (%) C | H | N | Found (%) C | H | N |
|---|---|---|---|---|---|---|---|---|---|---|---|---|
| 5 | H | H | p-CO$_2$CH$_3$ | H | Br | C$_{14}$H$_{14}$N$_3$O$_3$Br<br>235 – 237 (Decomp.) | 47.74 | 4.01 | 11.93 | 47.82 | 3.97 | 12.16 |
| 6 | H | H | p-NO$_2$ | H | Br | C$_{12}$H$_{11}$N$_4$O$_3$Br<br>244 (Decomp.) | 42.48 | 3.28 | 16.52 | 42.37 | 3.28 | 16.55 |
| 7 | H | H | m-NO$_2$ | H | Br | C$_{12}$H$_{11}$N$_4$O$_3$Br<br>242 – 243 (Decomp.) | 42.48 | 3.28 | 16.52 | 42.34 | 3.31 | 16.95 |
| 8 | H | H | p-CH$_3$ | H | Br | C$_{13}$H$_{14}$N$_3$OBr<br>269 – 270 (Decomp.) | 50.65 | 4.57 | 13.63 | 50.40 | 4.62 | 14.11 |
| 9 | H | H | o-CH$_3$ | H | Br | C$_{13}$H$_{14}$N$_3$OBr<br>268 – 269 (Decomp.) | 50.65 | 4.57 | 13.63 | 50.38 | 4.57 | 13.96 |
| 10 | H | H | p-Cl | H | Br | C$_{12}$H$_{11}$N$_3$OBrCl<br>245 – 246 (Decomp.) | 43.85 | 3.38 | 12.78 | 43.63 | 3.38 | 12.94 |
| 11 | H | H | m-Cl | H | Br | C$_{12}$H$_{11}$N$_3$OBrCl<br>255 (Decomp.) | 43.85 | 3.38 | 12.78 | 43.65 | 3.37 | 13.11 |
| 12 | H | H | m-Cl | p-Cl | Br | C$_{12}$H$_{10}$N$_3$OBrCl$_2$<br>268 – 269 (Decomp.) | 39.69 | 2.78 | 11.57 | 39.69 | 2.75 | 11.84 |
| 13 | H | H | p-F | H | Br | C$_{12}$H$_{11}$N$_3$OBrF<br>218 – 220 (Decomp.) | 46.16 | 3.56 | 13.46 | 45.82 | 4.01 | 13.12 |
| 14 | H | H | p-NH$_2$ | H | Br | C$_{12}$H$_{13}$N$_3$OBr<br>283 – 284 (Decomp.) | 46.60 | 4.24 | 18.11 | 46.97 | 4.28 | 18.43 |
| 15 | H | CH$_3$ | p-SO$_2$CH$_3$ | H | Br | C$_{14}$H$_{16}$N$_3$O$_3$SBr<br>241 – 143 (Decomp.) | 43.53 | 4.18 | 10.88 | 43.36 | 4.23 | 10.98 |
| 16 | CH$_3$ | H | p-SO$_2$CH$_3$ | H | Br | C$_{14}$H$_{16}$N$_3$O$_3$SBr<br>289 – 290 (Decomp.) | 42.43 | 4.06 | 10.60 | 42.69 | 4.22 | 10.97 |
| 17 | CH$_3$ | CH$_3$ | p-SO$_2$CH$_3$ | H | Br | C$_{15}$H$_{18}$N$_3$O$_3$SBr<br>263 – 264 (Decomp.) | 45.02 | 4.54 | 10.50 | 44.82 | 4.56 | 10.61 |

What is claimed is:

1. A 4-aminopyrimidium compound represented by the formula:

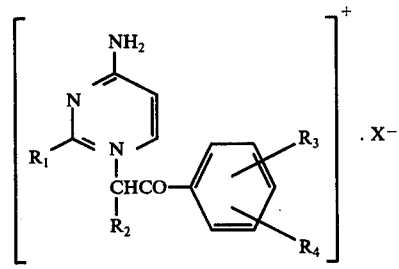

wherein $R_1$ and $R_2$ each represents hydrogen or methyl, $R_3$ represents a methylsulfonyl, methoxycarbonyl, nitro, methyl, chlorine, fluorine or amino group, $R_4$ is hydrogen or chlorine and X is bromine.

2. 4-Aminopyrimidium N$^1$-(p-methoxyphenacyl)bromide.

3. 4-Aminopyrimidium N$^1$-(m-methylphenacyl)bromide.

4. 4-Aminopyrimidium N$^1$-phenacyl bromide.

* * * * *